United States Patent
Kunz et al.

(10) Patent No.: US 8,461,382 B2
(45) Date of Patent: Jun. 11, 2013

(54) IONIC LIQUIDS

(75) Inventors: Werner Kunz, Regensburg (DE); Stefan Thomaier, Regensburg (DE); Eva Maurer, Deggendorf (DE); Oliver Zech, Regensburg (DE); Matthias Kellermeier, Altmannstein (DE); Regina Klein, Regensburg (DE)

(73) Assignee: BASF SE, Ludwigshafen (DE)

( * ) Notice: Subject to any disclaimer, the term of this patent is extended or adjusted under 35 U.S.C. 154(b) by 511 days.

(21) Appl. No.: 12/599,009

(22) PCT Filed: Apr. 30, 2008

(86) PCT No.: PCT/EP2008/055314
§ 371 (c)(1),
(2), (4) Date: Dec. 16, 2009

(87) PCT Pub. No.: WO2008/135482
PCT Pub. Date: Nov. 13, 2008

(65) Prior Publication Data
US 2010/0137175 A1    Jun. 3, 2010

(30) Foreign Application Priority Data

May 5, 2007 (DE) .......................... 10 2007 021 197
Dec. 19, 2007 (EP) ...................................... 07123577

(51) Int. Cl.
*C07C 59/125* (2006.01)

(52) U.S. Cl.
USPC .......................................... 562/587; 562/588

(58) Field of Classification Search
USPC ................................................ 562/587, 588
See application file for complete search history.

(56) References Cited

U.S. PATENT DOCUMENTS

| | | | |
|---|---|---|---|
| 5,233,087 A | 8/1993 | Cripe | |
| 5,798,329 A | 8/1998 | Taylor et al. | |
| 6,326,514 B1 | 12/2001 | Klug et al. | |
| 2004/0067202 A1* | 4/2004 | Looker et al. | 424/43 |
| 2007/0142646 A1 | 6/2007 | Maase et al. | |

FOREIGN PATENT DOCUMENTS

| | | |
|---|---|---|
| DE | 42 25 626 | 2/1994 |
| DE | 199 28 128 | 11/2000 |
| DE | 10 2004 027 329 | 12/2005 |
| EP | 0 715 072 | 6/1996 |
| EP | 0 716 072 | 6/1996 |
| EP | 0716072 A1 * | 6/1996 |
| WO | 97 28238 | 8/1997 |
| WO | 01 77081 | 10/2001 |
| WO | 02 24623 | 3/2002 |
| WO | 2005 070896 | 8/2005 |
| WO | 2007 057235 | 5/2007 |
| WO | 2007 057403 | 5/2007 |

OTHER PUBLICATIONS

Rogers, R. D. et al., "Ionic Liquids-Solvents of the Future?", Science, www.SCIENCEMAG.ORG., vol. 302, pp. 792-793 (Oct. 31, 2003) XP002494444.

Wasserscheid, P. et al., "Ionische Fluessigkeiten-neue., Loesungen fuer die Uebergangsmetallkatalyse", Angew. Chem, vol. 112, pp. 3927-3945 (2000).

Meindersma, W. G. et al., "Ionic Liquids", Ullmann's Encyclopedia of Industrial Chemistry, Electronic Release , 7$^{th}$ Edition, pp. 1-33 (2007).

* cited by examiner

*Primary Examiner* — Joseph Kosack
(74) *Attorney, Agent, or Firm* — Oblon, Spivak, McClelland, Maier & Neustadt, L.L.P.

(57) ABSTRACT

Novel ionic liquids comprising polyethercarboxylates as anions, a process for preparing them and their use.

31 Claims, No Drawings

IONIC LIQUIDS

The present invention relates to novel ionic liquids comprising polyethercarboxylates as anions, a process for preparing them and their use.

To a person skilled in the art, ionic liquids are liquids which consist exclusively of ions and have a melting point of less than 100° C. Examples of typical cations in ionic liquids comprise tetraalkylammonium, tetraalkylphosphonium, dialkylimidazolium or alkylpyridinium cations and examples of typical anions comprise trifluoromethanesulfonate, tetrafluoroborate, alkylsulphonates or bis(trifluoromethyl-sulfonyl)imide). Ionic liquids have become increasingly important in recent years. They have been proposed, for example, for use as solvents, as heat transfer media, as electrolytes in batteries, in double-layer capacitors, in solar cells or for use in extraction or separation processes. An overview of ionic liquids may be found, for example, in P. Wasserscheid, W. Keim, Angew. Chem. 2000, 112, 3926 to 3945 or in "Ionic Liquids", Ullmann's Encyclopedia of Industrial Chemistry, Electronic Release, 7th Edition, Wiley-VCH, Weinheim, N.Y. 2007.

WO 2005/070896 and WO 2007/057403 disclose the use of anions $R^a$—$S^-$ as anions in ionic liquids. Here, $S^-$ can be one of various acid groups such as sulfonates, sulfites, phosphonates, phosphites or carboxyl groups. The radical $R^a$ can be one of a wide variety of optionally substituted hydrocarbon radicals, including alkyl ether or alkyl polyether groups. Specific radicals R disclosed are 5-methoxy-3-oxapentyl, 8-methoxy-3,6-dioxaoctyl, 11-methoxy-3,6,9-trioxaundecyl, 7-methoxy-4-oxaheptyl, 11-methoxy-4,8-dioxaundecyl, 15-methoxy-4,8,12-trioxapentadecyl, 9-methoxy-5-oxanonyl, 14-methoxy-5,10-oxatetradecyl and also the corresponding ethoxy and hydroxy derivatives. However, specific combinations of these radicals with particular acid groups and particular cations are not disclosed.

U.S. Pat. No. 5,233,087 discloses alkylpolyethoxycarboxylates of the general formula $RO(CH_2CH_2O)_xCH_2COO^-M^+$, where R is a $C_8$-$C_{18}$-alkyl radical, x is from 1 to 15 and M is an alkali metal or alkaline earth metal ion. The alkylethoxycarboxylates are obtained by reaction of the corresponding alcohol $RO(CH_2CH_2O)_xH$ with chloroacetic acid. They are used as surfactants in aqueous solution.

EP 716 072 A1 discloses concentrated, flowable polyethercarboxylates of the general formula $RO(AO)_nCH_2COO^-M^+$, where R is a $C_8$-$C_{24}$-alkyl radical or an alkyl-substituted aryl radical having from 9 to 24 carbon atoms, n is from 1 to 15, A is $C_2$-$C_5$-alkylene and M is an alkali metal, ½ alkaline earth metal, ammonium or substituted ammonium ion. They can be used as dispersants and emulsifiers in the field of laundry detergents and cleaners.

Further examples of surfactants based on alkylpolyethercarboxylates are disclosed in WO 97/28238 or DE 10 2004 027 329 A1. Surfactants based on alkylpolyether-carboxylates are also commercially available, for example under the trade name Marke Akypo®. However, none of the documents mentioned discloses the use of such alkylpolyethercarboxylates in ionic liquids.

The fact that ionic liquids consists only of cations and anions explains their unique properties. They have, inter alia, a very low vapor pressure, can dissolve many organic and inorganic materials and display a high thermal stability. The physical and chemical properties of ionic liquids, for example melting point, thermal stability, viscosity, conductivity, solvation strength, solubility properties, acidity and coordination capability, are determined by the ions used, i.e. they can be varied in a targeted manner within a wide range by selection of cation and anion and matched to the particular use.

Ionic liquids are now also commercially available. In order to have the appropriate ionic liquid available for every process, there is great interest in synthesizing new ionic liquids. It was therefore an object of the invention to make novel ionic liquids available.

We have accordingly found an ionic liquid of the general formula $1/n[X^{n+}][Y^-]$ having a melting point of less than 100° C., where n is 1, 2 or 3 and
  the cation $X^{n+}$ is a cation selected from the group consisting of metal ions, quaternary ammonium, oxonium, sulfonium and phosphonium ions,
  the anion $Y^-$ has the general formula (II)

where
  x is from 2 to 8,
  $R^6$ is a branched on unbranched hydrocarbon group having from 1 to 3 carbon atoms,
  the radicals $R^7$ are each, independently of one another, a branched or unbranched alkylenic group having from 2 to 4 carbon atoms and
  $R^8$ is a branched or unbranched alkylenic group having from 1 to 4 carbon atoms, and the hydrogen atoms in the radicals $R^6$, $R^7$ and $R^8$ can in each case be completely or partly replaced by fluorine.

The following details may be provided about the invention:

In the following, "ionic liquids" are solvent-free, in particular water-free, compositions in the usual sense which have a melting point of less than 100° C. and are composed exclusively of cations and anions.

The ionic liquids of the invention have the general formula $1/n[X^{n+}][Y^-]$.

In the cations $X^{n+}$, n is 1, 2 or 3, preferably 1 or 2 and particularly preferably 1.

The cations can be metal ions, in particular alkali metal or alkaline earth metal ions. Examples of preferred metal ions comprise $Li^+$, $Na^+$, $K^+$, $Be^{2+}$, $Mg^{2+}$ and $Ca^{2+}$. Particular preference is given to $Na^+$ and $K^+$ and very particular preference is given to $Na^+$.

The cations $X^{n+}$ can also be quaternary ammonium, oxonium, sulfonium or phosphonium cations. Suitable cations of this type for use in ionic liquids are known to those skilled in the art, for example from WO 2007/057235, page 4, line 13 to page 18, line 38. A person skilled in the art will make an appropriate choice according to the desired properties of the ionic liquid.

The cations are preferably ammonium ions. These can be $NH_4^+$ or ammonium ions of aliphatic or aromatic amines, for example of nitrogen heterocycles. Examples of such compounds are given, in particular, in WO 2007/057235, page 5, line 14 to page 7, line 20.

To perform the present invention, preference is given to ammonium ions of the formulae (Ia), (Ib) ad (Ic)

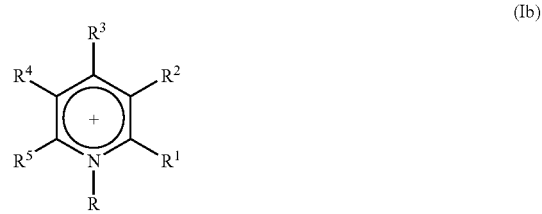

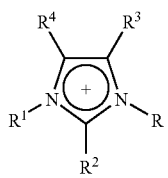
(Ic)

Preferred embodiments of the invention also comprise phosphonium ions of the general formula (Id) and sulfonium ions of the general formula (Ie).

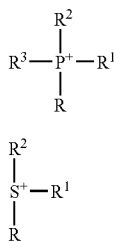

In the abovementioned formulae (Ia) to (Ie), the radicals R and also $R^1$ to $R^5$ are each, independently of one another, hydrogen or a saturated or unsaturated, acyclic or cyclic, aliphatic, aromatic or an araliphatic hydrocarbon radical having from 1 to 20 carbon atoms, where nonadjacent carbon atoms in the radicals can also be replaced by oxygen atoms and/or nitrogen atoms or the radicals may be substituted by functional groups. The hydrocarbon radicals are preferably saturated, aliphatic hydrocarbon radicals which may, if appropriate, be substituted as described. The radical R is in each case preferably hydrogen, methyl or ethyl and particularly preferably hydrogen.

Possible functional groups in the hydrocarbon radicals are in principle all functional groups which can be bound to a carbon atom. Suitable examples which may be mentioned are —OH (hydroxy), =O (in particular as carbonyl group), —$NH_2$ (amino), =NH (imino), —COOH (carboxy), —$CONH_2$ (carboxamide), —$SO_3H$ (sulfo) und —CN (cyano) and also fluorine, chlorine, bromine and iodine. Preferred functional groups are —OH and —COOH.

If nonadjacent carbon atoms in the hydrocarbon radicals are replaced by heteroatoms, these are preferably oxygen atoms. In other words, if there is any replacement at all, preference is given to radicals comprising ether groups —O—, hydroxy groups —OH and/or carboxyl groups —COOH.

Preferred ammonium ions of the formula (Ia) comprise those in which R is hydrogen, $R^1$ is a linear or branched, preferably linear, alkyl radical having from 1 to 20 carbon atoms, preferably from 4 to 20 carbon atoms, particularly preferably from 6 to 20 carbon atoms and very particularly preferably from 8 to 20 carbons atoms, and $R^2$ and $R^3$ are each, independently of one another, hydrogen, methyl or ethyl, preferably hydrogen or methyl. The properties of the ionic liquid, for example its melting point, can be controlled via the length of the radical $R^1$.

Further preferred ammonium ions (Ia) are those in which at least one of the radicals R, $R^1$, $R^2$ and $R^3$ is a radical which has from 1 to 20 carbon atoms, preferably from 2 to 20 carbon atoms, and is substituted by an OH group, preferably a terminal OH group. Preference is also given to monoethanolammonium, diethanolammonium or triethanolammonium ions, for example HO—$CH_2$—$CH_2$—$NH_3^+$, (HO—$CH_2$—$CH_2$—$)_2NH_2^+$, (HO—$CH_2$—$CH_2$—$)_3NH^{30}$ or HO—$CH_2$—$CH_2$—$N(CH_3)_3^+$ (choline). The radicals can optionally comprise further substituents, in particular —COOH. An example is carnitine $(H_3C)_3N^+$—$CH_2$—CH(OH)—$CH_2$—$COO^-$.

Preferred pyridinium ions (Ib) and imidazolium ions (Ic) comprise those in which at least one of the radicals R and $R^1$ to $R^4$ or $R^5$ is a linear or branched, preferably linear, alkyl radical having from 1 to 20 carbon atoms, preferably from 4 to 20 carbon atoms and particularly preferably from 6 to 20 carbon atoms, and the remaining radicals are each, independently of one another, hydrogen, methyl or ethyl, preferably hydrogen or methyl.

According to the invention, the anion $Y^{m-}$ has the general formula (II)

$$R^6O—(R^7—O—)_x—R^8—COO^-  \quad (II).$$

The radical $R^6$ is a straight-chain or branched hydrocarbon group which has from 1 to 3 carbon atoms and in which the hydrogen atoms may also be completely or partially replaced by fluorine. Preference is given to an alkyl radical selected from the group consisting of methyl, ethyl, n-propyl or i-propyl. Preference is given to a methyl or ethyl group and very particular preference is given to a methyl group.

The radical $R^6$ is bound via x alkoxy groups of the formula —$R^7$—O— to the group —$R^8$—$COO^-$ where the alkoxy groups in an anion can be identical or different.

The radicals $R^7$ are alkylene groups which have from 2 to 4 carbon atoms and in which the hydrogen atoms may also be completely or partially replaced by fluorine. Examples of $R^7$ comprise 1,2-ethylene groups —$CH_2$—$CH_2$—, 1,2-propylene groups —$CH_2$—CH($CH_3$)—, 1,3-propylene groups —$CH_2$—$CH_2$—$CH_2$—, 1,4-butylene groups —$CH_2$—$CH_2$—$CH_2$—$CH_2$— or 1,2-butylene groups —$CH_2$—CH($C_2H_5$)—. Preference is given to 1,2-ethylene groups —$CH_2$—$CH_2$— and/or 1,2-propylene groups —$CH_2$—CH($CH_3$)— and particular preference is given to 1,2-ethylene groups —$CH_2$—$CH_2$—. Preference is given to at least 50% of the alkylene groups being 1,2-ethylene groups. If the alkylene groups are branched, they can be incorporated in the orientation shown or in the converse orientation into the anion.

The radical $R^8$ is a branched or unbranched alkylene group which has from 1 to 4 carbon atoms and in which the hydrogen atoms may also be completely or partially replaced by fluorine. Examples comprise a methylene group —$CH_2$—, a 1,2-ethylene group —$CH_2$—$CH_2$—, a 1,2-propylene group —$CH_2$—CH($CH_3$)—, a 1,3-propylene group —$CH_2$—$CH_2$—$CH_2$—, a 1,4-butylene group —$CH_2$—$CH_2$—$CH_2$—$CH_2$— or a t-butylene group —$CH_2$—C($CH_3$)$_2$—. Preference is given to a methylene group —$CH_2$—.

The index x is from 2 to 8, preferably from 2 to 6, particularly preferably from 3 to 5 and very particularly preferably 3, and is, in a known way, the average for the alkoxy groups present, which of course does not have to be a natural number but can also be any rational number.

The properties of the ionic liquids of the invention can be influenced by a person skilled in the art via the choice of anions and cations. Of course, an ionic liquid can also comprise a plurality of different anions $Y^-$ and/or a plurality of different cations $X^{n+}$.

Without wishing to be tied to a particular theory, the particular properties of the ionic liquids of the invention appear to be at least influenced by chelate formation, as shown below by way of example for the case of a carboxyl group and a sodium ion.

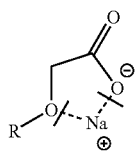

As a result of this internal chelate formation, the salt-like character of the ionic liquid decreases and the ionic liquid displays more nonpolar behavior. For example, the melting point of the ionic liquids of the invention is relatively low compared to other salts having similar cations and the solvent capability for nonpolar substances is good. The use of the anions according to the invention enables, for example, long-chain alkylimidazolium salts which are liquid at room temperature to be prepared.

Particular preference is given to ionic liquids composed of the anion $H_3CO\text{—}(CH_2\text{—}CH_2\text{—}O)_3\text{—}CH_2\text{—}COO^-$ (III) and cations selected from the group consisting of $K^+$, $NH_4^+$ or $R^1\text{—}NH_3^+$, where $R^1$ in this preferred variant is a linear alkyl radical having from 1 to 20, preferably from 4 to 20, particularly preferably from 6 to 18 and very particularly preferably from 8 to 18, carbon atoms. Examples of particularly preferred ions $R^1\text{—}NH_3^+$ in (III) comprise n-hexylammonium, n-octylammonium, n-decylammonium, n-dodecylammonium, n-tetradecylammonium, n-hexadecylammonium and n-octadecylammonium.

Further particularly preferred cations for the anion (III) are $Ca^{2+}$, $Mg^{2+}$, choline and also tetraalkylammonium ions, imidazolium ions and pyridinium ions which in each case have a linear alkyl radical $R^1$ having from 4 to 20, preferably from 6 to 18 and particularly preferably from 8 to 18, carbon atoms.

The ionic liquids of the invention can be prepared, for example, by firstly synthesizing the acids $R^6O\text{—}(R^7\text{—}O\text{—})_x\text{—}R^8\text{—}COOH$ (V) corresponding to the anion $R^6O\text{—}(R^7\text{—}O\text{—})_x\text{—}R^8\text{—}COO^-$ (II) and, in a second step, reacting the acid with a base comprising the cation or a precursor thereof. Any solvents used during the course of the synthesis are removed from the reaction system.

To synthesize the acids $R^6O\text{—}(R^7\text{—}O\text{—})_x\text{—}R^8\text{—}COOH$ (V), it is possible, for example, to start from the corresponding polyoxyalkylene monoalkyl ethers $R^6O\text{—}(R^7\text{—}O\text{—})_x\text{—}H$ (IV). These are reacted with a halocarboxylic acid of the general formula $Hal\text{—}R^8\text{—}COOH$ to form the carboxylic acid $R^6O\text{—}(R^7\text{—}O\text{—})_x\text{—}R^8\text{—}COON$ (V), where Hal is F, Cl, Br or I, preferably Cl, Br or I. Use of a ω-chlorocarboxylic acid of the general formula $Cl\text{—}R^8\text{—}COOH$ can be preferred, and in a particularly preferred variant of the synthesis chloroacetic acid is used. The reaction can be carried out by reacting the water-free ether alcohol (IV) with elemental sodium to form the more reactive alkoxide. The carboxylic acid (V) can be isolated by means of technologies known to those skilled in the art and be purified, for example, by vacuum distillation.

The carboxylic acids (V) can be neutralized by means of appropriate bases in a second step. Solvents in which the base may have been dissolved are subsequently separated off by distillation. The preparation of the sodium salt can be carried out, for example, by neutralization with the appropriate amount of aqueous NaOH followed by removal of the water under reduced pressure. It can also be carried out under anhydrous conditions by reaction of the carboxylic acid (V) with sodium hydrogencarbonate in an alcohol followed by removal of the alcohol by distillation.

Ionic liquids having ammonium ions (Ia), (Ib) or (Ic) in which R is hydrogen can be prepared in a simple manner by adding the corresponding unprotonated amine, if appropriate as a solution in a suitable solvent, to the carboxylic acid (V). If fully alkylated ammonium ions are to be used as bases, the ammonium ions can be used in the form of the corresponding hydroxides, for example as tetraalkylammonium hydroxides $NR_4^+$ $OH^-$. In place of the hydroxides, it is also possible to use the corresponding tetraalkylammonium halides and replace the halide ions by hydroxide ions by means of an ion exchanger in a second step. Imidazoles can, for example, firstly be converted into imidazolium carbenes by means of strong bases, e.g. potassium tert-butoxide, according to the process described in WO 01/77081. The imidazolium carbenes can then be brought into contact with the acids (V) to form the carboxylic acid anions and the corresponding imidazolium cations.

The ionic liquids of the invention have a melting point of less than 100° C., preferably less than 75° C. and particularly preferably less than 60° C. The melting point can be determined according to the desired melting point by choice of appropriate anions and cations. Ionic liquids which are liquid at room temperature can also be provided easily.

The ionic liquids of the invention can be used, in particular, as solvents or extractants.

They differ from other ionic liquids in that they have a greater ability to complex cations. Furthermore, they do not comprise any toxic components and have a very high electrochemical stability. The ionic liquids of the invention are particularly useful as solvents for carrying out chemical reactions, in particular for carrying out metathesis reactions, or else solvents for natural and synthetic polymers. Here, they display, depending on the composition, the properties of classical solvents, of hydrotropes or of surfactants.

They can also be used as extractants for liquid-liquid extraction, for example for the extraction of heavy metals, pharmacologically active substances, natural compounds, foodstuffs or food additives.

They can also be used as nonaqueous electrolytes or components of nonaqueous electrolytes in energy storage systems, for example batteries, or energy conversion systems, for example solar cells. In addition, they are suitable as solvents for electrochemical processes such as electrochemical deposition of metals.

Further uses comprise use as solvent and/or structuring matrix in nanoparticle synthesis, use for stabilizing nanoparticles or as solvent for natural and synthetic polymers.

It goes without saying that the ionic liquids of the invention can also be mixed with other ionic liquids in order to be used. In this way, further ionic liquids having a novel property spectrum can be obtained.

The ionic liquids of the invention have a number of advantages when used as solvents and extractants:

The ionic liquid allows solutions of salts in a nonaqueous, aprotic medium to be provided. Such solutions can be used advantageously in electrochemical processes, for example the electrochemical deposition of metals, since not every metal can be deposited from an aqueous medium. The cyclovoltammogram of the ionic liquids of the invention displays a wide voltage range and thus a high redox stability. They are therefore particularly useful for electrochemical applications.

As a result of their aprotic character, the ionic liquids are suitable as reaction medium for chemical reactions in the course of which salt-like or polar substances have to be kept in solution but which would at the same time be adversely affected by the presence of protic groups, for example OH groups or water.

Furthermore, ionic liquids have electrical conductivity without comprising water and as a result come into question for many industrial processes in which water-free liquids having a high dielectric constant have to be used.

The ionic liquids of the invention have a low volatility. Low-volatility solvents are of interest in industrial plants in which it is necessary to achieve low pressures (e.g. pumps). Furthermore, the Na+ and K+ salts, in particular, have very high decomposition points and a low corrosivity. They are therefore particularly suitable for high-temperature applications, e.g. for high-temperature lubrication or in the production of circuit boards.

The following examples illustrate the invention:

EXAMPLE 1

Synthesis of sodium 2,5,8,11-tetraoxatridecan-13-oate (TEGMECH2COO⁻Na⁺.

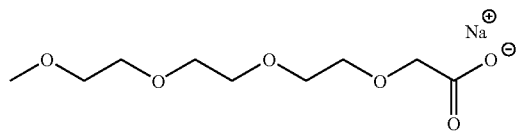

1st Step: Preparation of the Polyethercarboxylic Acid:

15.3 g of Na are dissolved in 260 ml of triethylene glycol monomethyl ether under a protective gas atmosphere while stirring vigorously. The dissolution is firstly carried out at room temperature and the mixture is later heated gradually to about 120° C. After complete dissolution of the Na, the solution is cooled to 100° C. and 30.9 g of chloroacetic acid dissolved in 60 ml of triethylene glycol monomethyl ether are added dropwise. The reaction mixture is then stirred at 100° C. for about 12 hours.

Excess triethylene glycol monomethyl ether is then distilled off in an oil pump vacuum (about $10^{-3}$ mbar) (boiling point: about 88-90° C.). The cooled residue is subsequently admixed with about 150 ml of water and, after stirring briefly, with 23 ml of 85% strength phosphoric acid. The now clear brown solution is extracted with 3×200 ml of dichloromethane. The combined organic phases are dried over magnesium sulfate. Filtration and removal of the solvent finally gives a dark brown oily liquid.

The crude 2,5,8,11-tetraoxatridecan-13-oic acid is purified by distilling it twice in an oil diffusion pump vacuum (about $10^{-7}$ mbar; boiling point: 135-145° C.). A colorless viscous liquid is obtained in the end.

2nd Step: Conversion into the Na Salt

The sodium salt of 2,5,8,11-tetraoxatridecan-13-oic acid is obtained by reacting the acid with equimolar amounts of aqeous 0.1M sodium hydroxide solution. The water is taken off on a rotary evaporator after neutralization. The product id dried successively in an oil pump vacuum, an oil diffusion pump vacuum and a turbomolecular pump vacuum (for a few days in each case).

As an alternative, the compound sodium 2,5,8,11-tetraoxatridecan-13-oate can also be prepared by a nonaqueous route by reaction of equimolar amounts of 2,5,8,11-tetraoxatridecan-13-oic acid and sodium hydrogen carbonate in ethanol. Drying is carried out in a manner analogous to the aqueous synthesis.

In a third variant, the polyethercarboxylic acid can be titrated in aqueous solution with NaOH standard solution just to the equivalance point (by means of pH measurement). This method avoids inaccuracies in the weighing of the two components, so that equimolarity is reliably ensured. The work-up is carried out as described above.

Sodium 2,5,8,11-tetraoxatridecan-13-oate is miscible in any ratio with water, dichloromethane, pentanol and acetone and partially miscible with diethyl ether. The viscosity at 25° C. at a low shear rate is in the order of one million millipascal seconds. The melting point is shown in Table 1.

EXAMPLE 2

Synthesis of lithium 2,5,8,11-tetraoxatridecan-13-oate (TEGMECH2COO⁻Li⁺)

The procedure of example 1 is repeated using LiOH for neutralization. The melting point is shown in Table 1.

EXAMPLE 3

Synthesis of potassium 2,5,8,11-tetraoxatridecan-13-oate (TEGMECH2COO⁻K⁺)

The procedure of example 2 is repeated using KOH for neutralization. The melting point is shown in Table 1.

EXAMPLE 4

Synthesis of calcium di(2,5,8,11-tetraoxatridecan-13-oate) ((TEGMECH2COO⁻)₂Ca²⁺)

The procedure of example 2 is repeated using CaCO₃ for neutralization. The melting point is shown in Table 1.

EXAMPLE 5

Synthesis of hexylammonium 2,5,8,11-tetraoxatridecan-13-oate

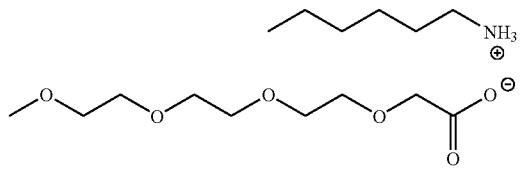

2,5,8,11-Tetraoxatridecan-13-oic acid is prepared as described in example 1. The alkylammonium salts can generally be obtained by direct reaction of the acid with equimolar amounts of the corresponding amine.

To synthesize hexylammonium 2,5,8,11-tetraoxatridecan-13-oate, 2,5,8,11-tetraoxatridecan-13-oic acid is neutralized with n-hexylamine. The reaction can be carried out either in the absence of a solvent (e.g. dropwise addition of pure hexylamine to the ether carboxylic acid, with cooling) or in organic solvents (typically ethanol). To avoid a backreaction and evaporation of the amine during drying in a high vacuum, the compounds are dried for only about one day in an oil pump vacuum. Since the syntheses are carried out in the absence of water and no water is formed during the neutralization, this mild drying is sufficient here. The melting point is shown in Table 1.

The viscosity of the ammonium salt is significantly lower than that of the sodium salt and is in the order of 20 000 mPas. It is thus comparable with the viscosity of honey or syrup. It can be concluded from electrical conductivity and fluorescence measurements that the ionic liquid of example 5 has hydrotropic character in aqueous solution.

EXAMPLE 6

Synthesis of dodecylammonium 2,5,8,11-tetraoxatridecan-13-oate

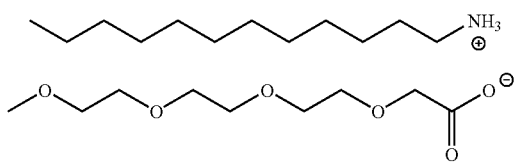

The procedure of example 4 is repeated using n-dodecylamine for neutralization.

It can be concluded from measurements of the electrical conductivity and the surface tension in aqueous medium that the ionic liquid of example 6 has surfactant character. Owing to the amphiphilic and thus solubilizing properties, the ionic liquid of example 6 has a wider solvent spectrum than conventional ionic liquids. Furthermore, it can be concluded that the ionic liquid of example 6 has structuring properties in water, organic solvents and in particular also in the pure state. Accordingly, it can serve, for example, as template in the mineralization processes (e.g. for mesoporous silicates). Furthermore, the ionic liquid of example 6 is liquid at room temperature (for melting point, see Table 1). Owing to this very low melting point, the ionic liquid mixes with water in any ratio to give a low-viscosity liquid, in contrast to classical ionic surfactants in the case of which highly viscous liquid-crystalline phases are formed at high surfactant concentrations in water.

EXAMPLES 7 to 11

Synthesis of further alkylammonium 2,5,8,11-tetraoxatridecan-13-oates

The procedure of example 5 was repeated using the following amines:
example 7: n-octylamine
example 8: n-decylamine
example 9: n-tetradecylamine
example 10: n-hexadecylamine
example 11: n-octadecylamine The melting points, decomposition points and viscosities are shown in Table 1.

Summary of the Properties

Table 1:

Melting and decomposition points (commencement of decomposition) and viscosities of various 2,5,8,11-tetraoxatridecan-13-oates.

[1] All liquids examined behaved as Newtonian fluids
n.d. not determined

Table 1 shows that the melting points of the ionic liquids increase with the increasing chain length of the alkyl radical in the anion. The melting point can thus be set in a targeted manner by choice of the chain length.

Likewise, the decomposition point and the viscosity can be influenced by the choice of the cation.

Use of the Ionic Liquids

Solubility experiments were carried out using the sodium 2,5,8,11-tetraoxatridecan-13-oate synthesized as described in example 1.

Ammonium nitrate is readily soluble in TEGMECH$_2$COONa even at room temperature, while NaCl dissolves in low concentrations at temperatures above 100° C. At 120° C., magnesium sulfate is appreciably soluble in TEGMECH$_2$COONa. The solubility of olive oil in a concentration of up to 10% by weight in TEGMECH2COONa is particularly worthy of mention with regard to the environmental compatibility of the sodium salt.

The invention claimed is:

1. An ionic liquid of the general formula $^1/n[X^{n+}][Y^-]$ having a melting point of less than 100° C., where n is 1, 2 or 3 and
the cation $X^{n+}$ is a cation selected from the group consisting of metal ions,
quaternary ammonium, oxonium, sulfonium and phosphonium ions,
the anion $Y^-$ has the general formula (II)

where
x is from 2 to 8,
$R^6$ is a 1 to 3 carbon atom branched or unbranched hydrocarbon group,
the radicals $R^7$ are each, independently of one another, a 2 to 4 carbon atom branched or unbranched alkylenic group and
$R^8$ is a 1 to 4 carbon atom branched or unbranched alkylenic group,
and the hydrogen atoms in the radicals $R^6$, $R^7$ and $R^8$ can in each case be completely or partly replaced by fluorine.

| | Cation | Melting point [° C.] | Decomposition point [° C.] | Viscosity[1] [mPa · s] at 25° C. |
|---|---|---|---|---|
| Example 2 | Li$^+$ | glass transition temperature <−20 | n.d. | n.d. |
| Example 1 | Na$^+$ | glass transition temperature −51.6 | 384 | 1.64 · 10$^5$ |
| Example 3 | K$^+$ | 59.1 | 369 | n.d. |
| Example 4 | Ca$^{2+}$ | glass transition temperature −80 | 320 | n.d. |
| Example 5 | n-hexylammonium | solidification at from −20 to +16 | n.d. | 2.40 · 10$^2$ |
| Example 7 | n-octylammonium | solidification at from −20 to +16 | 145 | 3.75 · 10$^2$ |
| Example 8 | n-decylammonium | 14 | 156 | 4.00 · 10$^2$ |
| Example 6 | n-dodecylammonium | 22 | 165 | 4.67 · 10$^2$ |
| Example 9 | n-tetradecylammonium | 38 | 170 | n.d. |
| Example 10 | n-hexadecylammonium | 47 | 175 | n.d. |
| Example 11 | n-octadecylammonium | 55 | 182 | n.d. |

2. The ionic liquid according to claim 1, wherein the cation is at least one cation selected from the group consisting of alkaline metal ions, alkaline earth metal ions, ammonium ions of the formulae (Ia), (Ib) and (Ic)

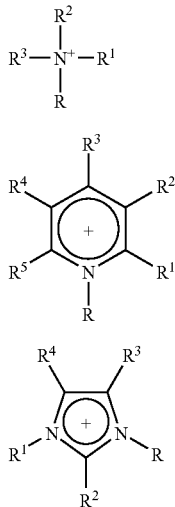

phosphonium ions of the general formula (Id) and sulfonium ions of the general formula (Ie)

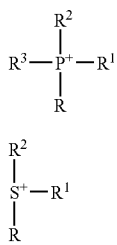

where the radicals R and $R^1$ to $R^5$ are each, independently of one another, hydrogen or a 1 to 20 carbon atom saturated or unsaturated, acyclic or cyclic, aliphatic, aromatic or araliphatic hydrocarbon radical, where nonadjacent carbon atoms in the radicals may also be replaced by oxygen atoms and/or nitrogen atoms or the hydrogen atoms of the radical may be substituted by functional groups.

3. The ionic liquid according to claim 2, wherein the cation is at least one cation selected from the group consisting of alkali metal ions, alkaline earth metal ions and ammonium ions of the formula (Ia).

4. The ionic liquid according to claim 3, wherein the cations are ammonium ions (Ia) in which R is hydrogen, $R^1$ is a 1 to 20 carbon atom linear or branched alkyl radical and $R^2$ and $R^3$ are each, independently of one another, hydrogen, methyl or ethyl.

5. The ionic liquid according to claim 4, wherein $R^1$ is a 8 to 20 carbon atom linear alkyl radical.

6. The ionic liquid according to claim 3, wherein the cations are ammonium ions (Ia) in which at least one of the radicals R, $R^1$, $R^2$ and $R^3$ is 1 to 20 carbon atom a radical and is substituted by an OH group and optionally a COOH group.

7. The ionic liquid according to claim 1, wherein $R^6$ is a methyl group.

8. The ionic liquid according to claim 1, wherein at least 50% of the groups $R^7$ are 1,2-ethylene groups.

9. The ionic liquid according to claim 1, wherein x is from 3 to 5.

10. The ionic liquid according to claim 1, wherein $R^8$ is a methylene group —$CH_2$—.

11. The ionic liquid according to claim 1, wherein the cation is $Li^+$, $Na^+$, $K^+$, $NH_4^+$ or an ammonium ion of the general formula $R^1$—$NH_3^+$, where $R^1$ is a 1 to 20 carbon atom linear alkyl radical, and the anion is $H_3CO$—(—$CH_2$—$CH_2$—O—$)_3$—$CH_2$—$COO^-$.

12. The ionic liquid according to claim 11, wherein $R^1$ is a 8 to 20 carbon atom linear alkyl radical.

13. A process for preparing an ionic liquid according to claim 1, wherein
a polyoxyalkylene monoalkyl ether $R^6O$—($R^7$—O—$)_x$—H (IV) is reacted with a halocarboxylic acid of the general formula Hal-$R^8$—COOH, where Hal is F, Cl, Br or I, in a first reaction to form the carboxylic acid $R^6O$—($R^7$—O—$)_x$—$R^8$—COOH (V) and
the carboxylic acid $R^6O$—($R^7$—O—$)_x$—$R^8$—COOH (V) formed is neutralized with a base $X(OH)_n$ or [X-nH] in a second reaction to form the ionic liquid $^1/n[X^{n+}][R^6O$—($R^7$—O—$)_x$—$R^8$—$COO^-$],
with the proviso that solvents used and/or solvents formed during the process are separated off completely.

14. The process according to claim 13, wherein the halocarboxylic acid is chloroacetic acid.

15. A solvent comprising the ionic liquid according to claim 1.

16. An extractant for liquid-liquid extraction comprising the ionic liquid according to claim 1.

17. An electrolyte or a component of nonaqueous electrolytes in energy storage systems and energy conversion systems comprising the ionic liquid according to claim 1.

18. A high-temperature lubricant comprising the ionic liquid according to claim 1.

19. An ionic liquid of the general formula $^1/n[X^{n+}][Y^-]$ having a melting point of less than 100° C., where n is 1, 2 or 3 and
the cation $X^{n+}$ is a metal ion,
the anion $Y^-$ has the general formula (II)

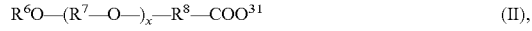

$$R^6O—(R^7—O—)_x—R^8—COO^{31} \qquad (II),$$

where
x is from 2 to 8,
$R^6$ is a 1 to 3 carbon atom branched or unbranched hydrocarbon group,
the radicals $R^7$ are each, independently of one another, a 2 to 4 carbon atom branched or unbranched alkylenic group and
$R^8$ is a 1 to 4 carbon atom branched or unbranched alkylenic group,
and the hydrogen atoms in the radicals $R^6$, $R^7$ and $R^8$ can in each case be completely or partly replaced by fluorine.

20. The ionic liquid according to claim 19, wherein the cation is at least one cation selected from the group consisting of alkaline metal ions and alkaline earth metal ions.

21. The ionic liquid according to claim 19, wherein $R^6$ is a methyl group.

22. The ionic liquid according to claim 19, wherein at least 50% of the groups $R^7$ are 1,2-ethylene groups.

23. The ionic liquid according to claim 19, wherein x is from 3 to 5.

24. The ionic liquid according to claim 19, wherein $R^8$ is a methylene group —$CH_2$—.

25. The ionic liquid according to claim 19, wherein the cation is $Li^+$, $Na^+$, $K^+$ or $NH_4^+$, and the anion is $H_3CO-(-CH_2-CH_2-O-)_3-CH_2-COO^-$.

26. A process for preparing an ionic liquid according to claim 19, wherein a polyoxyalkylene monoalkyl ether $R^6O-(R^7-O-)_x-H$ (IV) is reacted with a halocarboxylic acid of the general formula $Hal-R^8-COOH$, where Hal is F, Cl, Br or I, in a first reaction to form the carboxylic acid $R^6O-(R^7-O-)_x-R^8-COOH$ (V) and the carboxylic acid $R^6O-(R^7-O-)_x-R^8-COOH$ (V) formed is neutralized with a base $X(OH)_n$ or [X-nH] in a second reaction to form the ionic liquid $^1/_n[X^{n+}][R^6O-(R^7-O-)_x-R^8-COO^-]$, with the proviso that solvents used and/or solvents formed during the process are separated off completely.

27. The process according to claim 26, wherein the halocarboxylic acid is chloroacetic acid.

28. A solvent comprising the ionic liquid according to claim 19.

29. An extractant for liquid-liquid extraction comprising the ionic liquid according to claim 19.

30. An electrolyte or a component of nonaqueous electrolytes in energy storage systems and energy conversion systems comprising the ionic liquid according to claim 19.

31. A high-temperature lubricant comprising the ionic liquid according to claim 19.

\* \* \* \* \*